United States Patent [19]
Rühl et al.

[11] Patent Number: 5,902,916
[45] Date of Patent: May 11, 1999

[54] PROCESS FOR REACTING AN ORGANIC COMPOUND IN THE PRESENCE OF A RUTHENIUM CATALYST FORMED IN SITU

[75] Inventors: Thomas Rühl, Frankenthal; Boris Breitscheidel, Limburgerhof; Franz Josef Bröcker, Ludwigshafen; Wolfgang Reif, Frankenthal; Jochem Henkelmann, Mannheim; Karl Heinz Brauch, Lampertheim; Andreas Henne, Neustadt, all of Germany

[73] Assignee: BASF Aktiengesellschaft, Ludwigshafen, Germany

[21] Appl. No.: 08/845,435

[22] Filed: Apr. 25, 1997

[30] Foreign Application Priority Data

Apr. 26, 1996 [DE] Germany ............. 196 16 822
Jun. 5, 1996 [DE] Germany ............. 196 22 705

[51] Int. Cl.$^6$ ........................................ C07C 5/10
[52] U.S. Cl. .......................... 585/266; 585/269
[58] Field of Search ............................ 585/266, 269

[56] References Cited

U.S. PATENT DOCUMENTS

| | | | |
|---|---|---|---|
| 2,606,925 | 8/1952 | Whitman | 260/563 |
| 2,822,392 | 2/1958 | Illich, Jr. et al. | 260/563 |
| 2,927,127 | 3/1960 | Somerville et al. | 260/488 |
| 3,520,928 | 7/1970 | Greco et al. | 260/563 |
| 3,591,635 | 7/1971 | Farrissey et al. | 260/563 |
| 3,636,108 | 1/1972 | Brake | 260/563 |
| 3,697,449 | 10/1972 | Brake | 252/474 |
| 3,832,401 | 8/1974 | Knifton et al. | 260/570.8 R |
| 4,273,680 | 6/1981 | Halluin et al. | 252/466 J |
| 4,273,939 | 6/1981 | Barnett et al. | 564/358 |
| 4,307,248 | 12/1981 | Barnett et al. | 564/358 |
| 4,318,829 | 3/1982 | Halluin et al. | 252/466 J |
| 4,429,155 | 1/1984 | Goetz et al. | 564/402 |
| 4,464,482 | 8/1984 | Bird et al. | 502/325 |
| 4,551,564 | 11/1985 | Otte et al. | 568/834 |
| 4,749,677 | 6/1988 | Fiato et al. | 502/325 |
| 4,914,239 | 4/1990 | Kiyuma et al. | 564/450 |
| 4,952,549 | 8/1990 | Immel et al. | 502/330 |
| 5,322,965 | 6/1994 | Immel et al. | 564/446 |

FOREIGN PATENT DOCUMENTS

| | | |
|---|---|---|
| 067 058 | 12/1982 | European Pat. Off. . |
| 2132547 | 6/1971 | Germany . |
| 6803180 | 2/1968 | Japan . |
| 7019901 | 7/1970 | Japan . |
| 7235424 | 9/1972 | Japan . |
| 9196843 | 11/1984 | Japan . |
| 137 526 | of 0000 | Poland . |

*Primary Examiner*—Gary Geist
*Assistant Examiner*—Brian J. Davis
*Attorney, Agent, or Firm*—Keil & Weinkauf

[57] ABSTRACT

A process for reacting an organic compound in the presence of a catalyst, wherein the catalyst comprises a homogeneous ruthenium compound or a mixture of two or more thereof deposited in situ on a support.

15 Claims, 1 Drawing Sheet

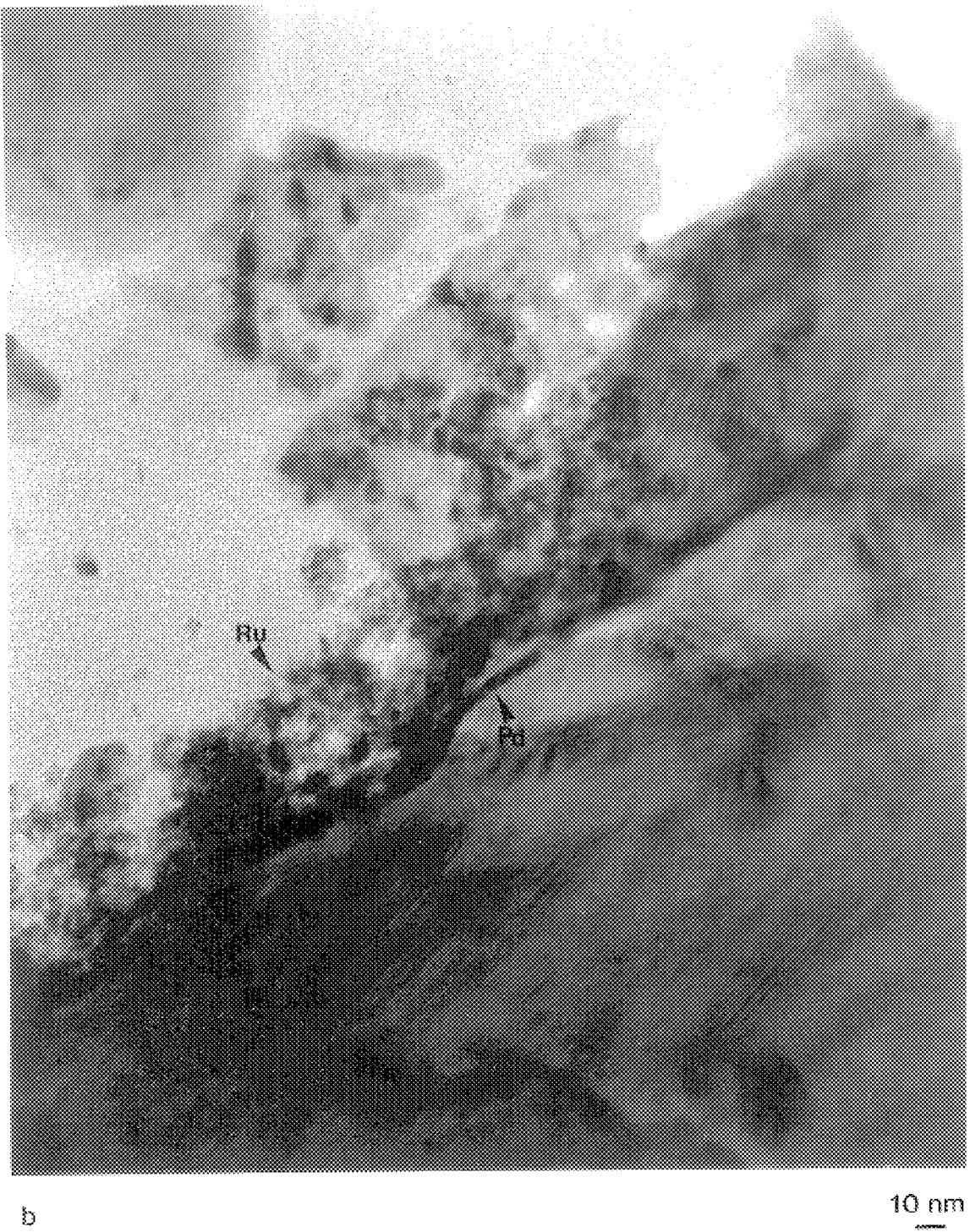

PROCESS FOR REACTING AN ORGANIC COMPOUND IN THE PRESENCE OF A RUTHENIUM CATALYST FORMED IN SITU

The present invention relates to a process for reacting an organic compound in the presence of a catalyst, wherein the catalyst comprises a homogeneous ruthenium compound or a mixture of two or more thereof deposited in situ on a support, and a supported catalyst, obtainable by a process wherein a homogeneous ruthenium compound or a mixture of two or more thereof is deposited on a support while passing a solution comprising the ruthenium compound or the mixture of two or more thereof through said support or along the same.

In one embodiment, the present invention provides a process for hydrogenating an aromatic compound in which at least one hydroxyl group is bonded to an aromatic ring and preferably, in addition to the hydroxyl group(s), at least one unsubstituted or substituted $C_1$–$C_{10}$-alkyl group and/or at least one $C_1$–$C_{10}$-alkoxy group is bonded to an aromatic ring. Furthermore, preference is given to using monoalkyl-substituted phenols in the process of the present invention. In this process, the monocyclic or polycyclic aromatic compounds are hydrogenated in the presence of the above-described catalyst to give the corresponding cycloaliphatic compounds, with the hydroxyl group being retained.

Cycloaliphatic alcohols, in particular alkylcyclohexanols, are important intermediates for producing various fragrances, drugs and other organic fine chemicals. These cycloaliphatic alcohols can be conveniently obtained by catalytic hydrogenation of the corresponding aromatic precursors.

Preparation of alkylcyclohexanols by catalytic hydrogenation of the corresponding alkylphenols is known. The hydrogenation of alkylphenols in the presence of hydrogenation catalysts, in particular catalysts applied to supports, to give the corresponding alkylcyclohexanols has been described many times.

Catalysts used are, for example, metallic rhodium, ruthenium, palladium and nickel on catalyst supports. Catalyst supports used are carbon, barium carbonate and in particular, aluminum oxide.

PL 137 526 describes the hydrogenation of p-tert-butylphenol to give p-tert-butylcyclohexanol using a nickel catalyst.

DE-A-34 01 343 and EP 0 141 054 describe a process for preparing 2- and 4-tert-butylcyclohexanol from 2- and 4-tert-butylphenol by catalytic hydrogenation. The hydrogenation is carried out in two stages, with a palladium catalyst on an $Al_2O_3$ support being used in the first stage and a ruthenium catalyst on an $Al_2O_3$ support being used in the second stage. The metal content on the support is here from 0.1 to 5% by weight. The supports are not further specified. The process is carried out at a pressure of 300 bar with recirculation of product, and the cis-tert-butylcyclohexanols are preferably obtained, with from 0.1 to 0.5% of by-products being formed.

U.S. Pat. No. 2 927 127 describes a process for preparing p-tert-butylcyclohexanol and esters thereof by catalytic hydrogenation of p-tert-butylphenol. Catalysts used are 5% rhodium on carbon, 5% palladium on barium carbonate and 5% ruthenium on carbon. When using ruthenium on carbon, the reaction was carried out at a pressure of from 70 to 120 bar and at from 74 to 93° C. 66% of the cis isomer were obtained as hydrogenation product.

DE-A-29 09 663 describes a process for preparing cis-alkylcyclohexanols by catalytic hydrogenation of the corresponding alkylphenols. The catalyst used was ruthenium on an $Al_2O_3$ support and the hydrogenation was carried out at a pressure of 40, 60 or 80 bar. The products obtained were predominantly cis-alkylcyclohexanols with from 0.1 to 1% of alkylbenzenes being formed as by-product.

In a further embodiment, the present invention provides a process for hydrogenating an aromatic compound in which at least one amino group is bonded to an aromatic ring and preferably, in addition to the amino group(s), at least one unsubstituted or substituted $C_1$–$C_{10}$-alkyl group and/or at least one $C_1$–$C_{10}$-alkoxy group is bonded to an aromatic ring. Particular preference is given to using monoalkyl-substituted amines.

The monocyclic or polycyclic aromatic compounds are here hydrogenated in the presence of the catalyst described in the introduction to give the corresponding cycloaliphatic compounds, with the amino group being retained.

Cycloaliphatic amines, in particular unsubstituted or substituted cyclohexylamines and dicyclohexylamines, are used for producing ageing inhibitors for rubbers and plastics, as corrosion inhibitors and also as intermediates for crop protection chemicals and textile auxiliaries. In addition, cycloaliphatic diamines are used in the preparation of polyamide and polyurethane resins and are also used as hardeners for epoxy resins.

The preparation of cycloaliphatic amines by catalytic hydrogenation of the corresponding monocyclic or polycyclic aromatic amines is known. The hydrogenation of aromatic amines in the presence of hydrogenation catalysts, in particular catalysts applied to supports, to give the corresponding cycloaliphatic amines has been described many times.

Catalysts used are, for example, Raney cobalt with basic additives (JP 43/3180), nickel catalysts (U.S. Pat. No. 4 914 239, DE 80 55 18), rhodium catalysts (BE 73 93 76, JP 70 19 901, JP 72 35 424) and also palladium catalysts (U.S. Pat. No. 3 520 928, EP 501 265, EP 53 181, JP59/196 843). However, ruthenium-containing catalysts are most used.

DE 21 32 547 discloses a process for hydrogenating monocyclic or polycyclic aromatic diamines to give the corresponding cycloaliphatic amines, this process being carried out in the presence of a suspended ruthenium catalyst.

EP 67 058 describes a process for preparing cyclohexylamine by catalytic hydrogenation of the corresponding aromatic amine. The catalyst used is ruthenium metal in a finely divided form on activated aluminum pellets. After four recirculations, the catalyst began to lose its effectiveness.

EP 324 984 relates to a process for preparing a mixture of unsubstituted or substituted cyclohexylamine and unsubstituted or substituted dicyclohexylamine by hydrogenation of unsubstituted or substituted aniline using a catalyst comprising ruthenium and palladium on a support, with the catalyst additionally containing an alkaline alkali metal compound as modifier. A process which is similar in principle is described in EP 501 265, where the catalyst contains niobic acid, tantalic acid or a mixture of both as modifier.

U.S. Pat. No. 2 606 925 describes a process for preparing an aminocyclohexyl compound by hydrogenation of a corresponding aromatic compound in the presence of a ruthenium catalyst whose catalytically active component is selected from the group consisting of elemental ruthenium, ruthenium oxides and ruthenium salts in which the ruthenium is present in the anion or in the cation. As the examples of this process show, the catalyst used is also prepared and dried in a separate stage and introduced into the reaction vessel after a relatively long drying time.

A further process for preparing cyclohexylamine is described in U.S. Pat. No. 2 822 392; this patent is directed mainly at the use of a specific reactor in which the aniline and the hydrogen as starting materials are reacted with one another in the countercurrent.

U.S. Pat. No. 3 636 108 and U.S. Pat. No. 3 697 449 concern the catalytic hydrogenation of an aromatic, nitrogen-containing compound using a ruthenium catalyst which additionally comprises an alkali metal compound as modifier.

Furthermore, the present invention in particular relates to a process for the hydrogenation of an organic compound, which exhibits at least one C=O-group, such as a ketone aldehyde, a carboxylic acid or a derivative thereof, or a mixture of two or more thereof.

U.S. Pat. No. 4 464 482 describes a ruthenium catalyst for hydrogenations consisting of a metal support having a specific structure, a coating of activated alumina deposited thereonto and an amount of ruthenium of 0.03 to 3% by weight put onto the coating by impregnation. The oxide layer is generated by impregnation of the support in a dispersion of activated alumina and subsequent tempering or—in case the metal support comprises aluminum—by tempering the same. Furthermore, this reference describes the use of this catalyst for several hydrogenations of in particular aldehydes and ketones.

As can be seen from the above summary of the prior art, the ruthenium catalyst used in the above- described processes was always prepared in a separate step. The catalyst is prepared by impregnating the catalyst support with the active component or spraying the active component onto the catalyst support, drying the catalyst and then calcining it at high temperatures. In most cases, the catalyst is subsequently activated at elevated temperature in a stream of hydrogen.

It is an object of the present invention to provide a process for reacting an organic compound as defined in the introduction, with very high yields or almost complete conversion being achieved. A further object of the invention is the provision of such a process in which only a minimal proportion of by-products or decomposition products is formed during the hydrogenation. In addition, it should be possible to carry out the process of the present invention without separation, work-up and recirculation of catalyst. It should also be possible to carry out the process at high throughput rates over the catalyst with a long catalyst operating life and giving an extremely high turnover number, with the corresponding hydrogenation products being obtained in high yield and high purity.

We have found that these objects are achieved by the process for reacting an organic compound and the use of the catalysts of the present invention, as defined above, for reacting organic compounds including low molecular weight (monomeric) and polymeric organic compounds (polymers) in the presence thereof.

A particular advantage of the invention is that the reaction product is free of traces of ruthenium and can be directly used further without removal of catalyst.

Furthermore, the process of the present invention gives high turnover numbers at high throughput rates over the catalyst and for long catalyst operating lives. Here, the throughout rate over the catalyst is the space-time yield of the process, ie. the amount of starting material converted per unit time and per amount of catalyst present. Operating life is the time for which the catalyst can be used or the amount of unreacted starting material which can be passed over a catalyst without its properties being impaired or the product properties changing significantly.

In the process as described herein, the respective reaction products are obtained in high yield and purity.

Furthermore, it has been found that the catalysts of the invention and the catalysts used according to the invention, respectively, allow to work under a liquid loading of 300 $m^3/m^2$ without impairing the mechanical properties. This results in that in case of optimum substance conversion, reactions, preferably hydrogenations, having extremely high heat tonality may be carried out safely.

COMPOUNDS

The term "organic compound" as used within the present invention comprises all organic compounds including low molecular weight (monomeric) and polymeric organic compounds which may be catalytically reacted, in particular those which exhibit groups which are treatable with hydrogen, such as C—C-double or C—C-triple bonds.

The present invention relates particularly to a process for reacting an organic compound in the presence of a catalyst, wherein the reaction is a hydrogenation, dehydrogenation, hydrogen analysis, aminating hydrogenation or dehalogenation, more preferably a hydrogenation.

In particular, organic compounds having one or more of the following structural units may be used:

(I)

C=C

(II)

C≡C

(III)

(IV)

C=N

(V)

C≡N

(VI)

C=O

(VII)

C=S

(VIII)

—NO$_2$

The process of the invention is particularly suitable for reacting, preferably hydrogenating, an organic compound which is selected from the group consisting of an aromatic compound in which at least one hydroxyl group is bonded to an aromatic ring, an aromatic compound in which at least one amino group is bonded to an aromatic ring, a ketone, an aldehyde, a carboxylic acid or a derivative thereof, a polymer comprising at least one C—C double bond, a polymer comprising at least one C=C-group, and a mixture of two or more thereof.

Within the process of the invention organic compounds comprising units of different structures, as defined above, may be reacted, such as organic compounds which exhibit C—C-multiple bonds and carbonyl groups, since the catalyst used within the process of the invention are capable to first selectively hydrogenate one of the two groups, i.e. to achieve a hydrogenation of these groups from about 90 to 100%, while at first the other groups are reacted, preferably hydrogenated, to an extent of less than 25% and in general 0 to about 7%. Generally, first the C—C-multiple bond and subsequently the C=O-group are reacted, e.g. hydrogenated, respectively.

The term "aromatic compound in which at least one hydroxyl group is bonded to an aromatic ring" or "aromatic compound in which at least one amino group is bonded to an aromatic ring" means all compounds which have a unit of the structure (I):

(I)

where R is a hydroxyl group or an amino group.

If, in the process of the present invention, use is made of aromatic compounds in which at least one hydroxyl group and also at least one unsubstituted or substituted $C_1-C_{10}$-alkyl radical and/or $C_1-C_{10}$-alkoxy radical is bonded to an aromatic ring, the resulting isomer ratio of cis to trans products can be varied within a wide range, depending on the reaction conditions (temperature, solvent). Furthermore, the compounds obtained can be processed further without further purification steps, since the formation of alkylbenzenes is virtually completely avoided.

Like the above-described compounds in which at least one hydroxyl group is bonded to an aromatic ring, aromatic compounds in which at least one amino group is bonded to an aromatic ring can also be hydrogenated by the process of the present invention to give the corresponding cycloaliphatic compounds with high selectivity. For the amines additionally substituted by a $C_1-C_{10}$-alkyl radical and/or $C_1-C_{10}$-alkoxy radical, what has been said above regarding the ratio of the cis and trans isomers also applies.

In particular, this embodiment virtually completely avoids the formation of deamination products such as cyclohexanes or partially hydrogenated dimerization products such as phenylcyclohexylamines.

In detail, the following compounds may be reacted with the process of the invention:

Aromatic compounds in which at least one hydroxyl group is bonded to an aromatic ring Aromatic compounds in which at least one hydroxyl group and preferably also at least one unsubstituted or substituted $C_1-C_{10}$-alkyl radical and/or alkoxy radical is bonded to an aromatic ring can be hydrogenated by means of the process of the present invention to give the corresponding cycloaliphatic compounds, with it also being possible to use mixtures of two or more of these compounds. The aromatic compounds used can be monocyclic or polycyclic aromatic compounds. The aromatic compounds contain at least one hydroxyl group bonded to an aromatic ring; the simplest compound of this group is phenol. The aromatic compounds preferably have one hydroxyl group per aromatic ring and can be substituted on the aromatic ring or rings by one or more alkyl and/or alkoxy radicals, preferably $C_1-C_{10}$-alkyl and/or alkoxy radicals, particularly preferably $C_1-C_{10}$-alkyl radicals, in particular methyl, ethyl, propyl, isopropyl, butyl, isobutyl and tert-butyl radicals; among the alkoxy radicals, preference is given to $C_1-C_8$-alkoxy radicals such as the methoxy, ethoxy, propoxy, isopropoxy, butoxy, isobutoxy and tert-butoxy radicals. The aromatic ring or rings and also the alkyl and alkoxy radicals may be unsubstituted or substituted by halogen atoms, in particular fluorine atoms, or other suitable inert substituents.

Preferably, the compounds which can be hydrogenated according to the present invention have at least one, preferably from one to four, in particular one, $C_1-C_{10}$-alkyl radical which is preferably located on the same aromatic ring as the hydroxyl group or groups. Preferred compounds are (mono)alkylphenols, where the alkyl radical can be in the o, m or p position relative to the hydroxyl group. Particular preference is given to trans-alkylphenols, also known as 4-alkylphenols, where the alkyl radical preferably has from 1 to 10 carbon atoms and is, in particular, a tert-butyl radical. Preference is given to 4-tert-butylphenol. Polycyclic aromatic compounds which can be used according to the present invention are, for example, β-naphthol and α-naphthol.

The aromatic compounds in which at least one hydroxyl group and preferably also at least one unsubstituted or substituted $C_1-C_{10}$-alkyl radical and/or alkoxy radical is bonded to an aromatic ring can also have a plurality of aromatic rings which are linked via an alkylene radical, preferably a methylene group. The alkylene group, preferably methylene group, which forms the linkage can have one or more alkyl substituents which can be $C_1-C_{20}$-alkyl radicals and are preferably $C_1-C_{10}$-alkyl radicals, particularly preferably methyl, ethyl, propyl, isopropyl, butyl or tert-butyl.

In these compounds, each of the aromatic rings can bear at least one bonded hydroxyl group. Examples of such compounds are bisphenols, which are linked in the 4 position via an alkylene radical, preferably a methylene radical.

In the process of the present invention, particular preference is given to reacting a phenol substituted by a $C_1-C_{10}$-alkyl radical, preferably $C_1-C_6$-alkyl radical, where the alkyl radical may be unsubstituted or substituted by an aromatic radical, or mixtures of two or more of these compounds.

In a further preferred embodiment of this process, p-tert-butylphenol, bis(p-hydroxyphenyl)dimethylmethane or a mixture thereof is reacted.

Aromatic compounds in which at least one amino group is bonded to an aromatic ring The process of the present invention also enables aromatic compounds in which at least one amino group is bonded to an aromatic ring to be hydrogenated to give the corresponding cycloaliphatic compounds, with mixtures of two or more of these compounds also being able to be used. The aromatic compounds can be monocyclic or polycyclic aromatic compounds. The aromatic compounds contain at least one amino group which is bonded to an aromatic ring. The aromatic compounds are preferably aromatic amines or diamines and can be substituted on the aromatic ring or rings or on the amino group by one or more alkyl and/or alkoxy radicals, preferably $C_1-C_{20}$-alkyl radicals, in particular methyl, ethyl, propyl, isopropyl, butyl, isobutyl and tert-butyl radicals. Among the alkoxy radicals, preference is given to $C_1-C_8$-alkoxy radicals such as methoxy, ethoxy, propoxy, isopropoxy, butoxy, isobutoxy and tert-butoxy radicals. The aromatic ring or rings and also the alkyl and alkoxy radicals can be unsubstituted or substituted by halogen atoms, in particular fluorine atoms, or other suitable inert substituents.

The aromatic compound in which at least one amino group is bonded to an aromatic ring can also have a plurality of aromatic rings which are linked via an alkylene group, preferably a methylene group. The alkylene group, preferably methylene group, which forms the linkage can bear one or more alkyl substituents which can be $C_1$–$C_{20}$-alkyl radicals and are preferably $C_1$–$C_{10}$-alkyl radicals, particularly preferably methyl, ethyl, propyl, isopropyl, butyl, sec-butyl or tert-butyl.

The amino group bonded to the aromatic ring may be unsubstituted or substituted by one or two of the above-described alkyl radicals.

Particularly preferred compounds are aniline, naphthylamine, diaminobenzenes, diaminotoluenes and bis-p-aminophenylmethane or mixtures thereof.

Compounds comprising C=O groups

Within the process of the invention it is also possible to react, in particular to hydrogenate, compounds comprising C=O groups, i.e. in particular aldehydes, ketones, carboxylic acids and their derivatives, such as carboxylic acid esters, carboxylic acid halides and carboxylic anhydrides, and mixtures of two or more of the above-mentioned compounds.

In particular aldehydes and ketones, preferably those having one to 20 C-atoms, such as formaldehyde, acetaldehyde, propionaldehyde, n-butyraldehyde, valeraldehyde, caproaldehyde, heptaldehyde, phenylacetaldehyde, acrolein, crotonaldehyde, benzaldehyde, o-, m-, p-tolualdehyde, salicylic aldehyde, anisaldehyde, vanillin, zinnamic aldehyde, acetone, methyl ethyl ketone, 2-pentanone, 3-pentanone, 2-hexanone, 3-hexanone, cyclohexanone, isophorone, methyl isobutyl ketone, mesityl oxide, acetophenone, propiophenone, benzophenone, benzalacetone, dibenzalacetone, benzalacetophenone, glycol aldehyde, glyoxal, 2,3-butandione, 2,4-pentandione, 2,5-hexandione, terephthalaldehyde, glutaraldehyde, diethylketone, methyl vinyl ketone, acetylacetone, 2-ethylhexanal, or mixtures of two ore more thereof, may be used.

Furthermore, also polyketones, such as copolymers of ethylene and CO are used.

Furthermore, carboxylic acids and derivatives thereof, preferably those having 1 to 20 C-atoms may be reacted. In particular, the following are to be mentioned:

Carboxylic acids, such as formic acid, acetic acid, propanoic acid, butanoic acid, iso-butanoic acid, n-valeric acid, pivalic acid, caproic acid, heptanoic acid, octanoic acid, decanoic acid, lauric acid, myristic acid, palmitic acid, stearic acid, acrylic acid, methacrylic acid, oleic acid, elaidic acid, linoleic acid, linolenic acid, cyclohexane carboxylic acid, benzoic acid, phenylacetic acid, o-, m-, p-toluylic acid, o-, p-chlortenzoic acid, o-, p-nitrobenzoic acid, salicylic acid, p-hydroxybenzoic acid, anthranilic acid, p-aminobenzoic acid, oxalic acid, malonic acid, succinic acid, glutaric acid, adipic acid, pimelic acid, suberic acid, azelaic acid, sebacic acid, maleic acid, fumaric acid, phthalic acid, isophthalic acid, teraphthalic acid, and mixtures of two or more thereof.

Carboxylic acid halides, such as the chlorides and bromides of the above-mentioned carboxylic acids, in particular acetylchloride or-bromide, stearic acid chloride or -bromide and benzoic acid chloride or -bromide, which are dehalogenated.

Carboxylic acid esters, such as the $C_1$- to $C_{10}$-alkyl esters of the above-mentioned carboxylic acids, particularly methyl formiate, acetic acid ester, butanoic acid butyl ester, dimethyl terephthalate, dimethyl adipate, methyl (meth) acrylate, butyrolactone, caprolactone and polycarboxylic acid esters, such as polyacrylic and polymethacrylic acid esters and copolymers and polyesters thereof, such as poly (methyl(meth)acrylates); these esters are in particular hydrogenated, i.e. the esters are reacted to the corresponding acids and alcohols.

Carboxylic anhydrides, such as anhydrides of the above-mentioned carboxylic acids, in particular acetic acid anhydride, propanoic acid anhydride, benzoic acid anhydride and maleic acid anhydride.

Carboxylic acid amides, such as amides of the above-mentioned is carboxylic acids, such as formamide, acetamide, propionic amide, stearamide and terephthalamide.

In addition thereto, also hydroxy carboxylic acids, such as lactic, malic acid, tartaric acid or citric acid, or amino acids, such as glycine, alanine, proline and arginine may be reacted.

Nitriles

Furthermore, also nitriles, preferably aliphatic or aromatic mono or dinitriles, such as acetonitrile, propionitrile, butyronitrile, stearic acid nitrile, isocrotonic acid nitrile, 3-butinnitrile, 2,3-butadiene nitrile, 2,4-pentadiene nitrile, 3-hexene-2,6-dinitrile, chloracetonitrile, trichloracetonitrile, lactic acid nitrile, phenol acetonitrile, 2-chlorbenzonitrile, 2,6-dichlorobenzonitrile, isophthalonitrile, particularly aliphatic alpha, omega-dinitriles, such as succinonitrile, glutaronitrile, adiponitrile, pimelicnitrile and suberic nitrile or aminonitriles, such as 4-amino butanoic acid nitrile, 5-aminopentanoic acid nitrile, 6-aminohexanoic acid nitrile, 7-aminoheptanoic acid nitrile and 8-aminooctanoic acid nitrile.

Furthermore, within the process according to the invention, the following reactions may be carried out:

The hydrogenation of aromatic compounds, such as benzene, toluenes, xylols, naphthalines and substituted derivatives thereof, leading to the corresponding alicyclic compounds; the hydrogenation of alkenes or alkines, such as ethylene, propylene, 1-, 2-butene, 1-, 2-, 3- and 4-octene, butadiene, and hexatriene leading to the corresponding alkanes; the hydrogenation of nitroalkanes, such as nitroethane, nitromethane, nitropropane and 1,1-dinitroethane leading to the corresponding amines; the hydrogenation of imines, such as quinone imines, ketimines, ketene imines or aliphatic imines, such as propioamine, hexane imine; the dehalogenation of organic compounds which contain halogen atoms, particularly of aromatic halogen-containing compounds, such as chloro- and bromobenzene, bromo- and chlorotoluenes and chloro- and bromo xylols, also including compounds with more than one halogen atoms substituted, may be used; the aminating hydrogenation of i.e. alcohols, such as vinyl alcohol.

Furthermore, within the process of the invention also oximes may be reacted or secondary amines may be prepared starting from ketones and primary amines.

The catalysts according to the invention may be also used for the hydrogenation, dehydrogenation, hydrogenolysis, aminating hydrogenation and dehalogenation of large molecules, preferably of polymers.

Accordingly, the present invention also relates to a process for reacting a polymer comprising at least one catalytically reactable group in the presence of the above identified catalyst, wherein the hydrogenation of polymers comprising C=O-groups, such as polyesters of dicarboxylic acids, unsaturated monocarboxylic acids, such as poly(meth) acrylates, olefin/CO-copolymers or polyketones is preferred.

In particular, the present invention relates to a process for the hydrogenation of a polymer comprising at least one C=O-group in the presence of the above-mentioned catalyst.

The term "polymer comprising at least one catalytically reactable group" relates to all polymers comprising such groups, in particular to polymers comprising units having the structures (I) to (VIII), as defined above with respect to the monomeric compounds, or a halogen atom. Needless to say that the referenced polymers comprise the respective unit at least once and that also one or more units of two or more of said structures may be present in the polymer reacted according to the invention.

The average molecular weight of the polymers to be reacted within the process of the invention is generally about 500 to about 500000, preferably about 1000 to about 100000 and more preferably about 1000 to about 50000.

As examples for polymers which are to be reacted, preferably hydrogenated, with the process of the invention, the following are to be mentioned:

Polymers having C—C-double bonds, e.g. polybutadienes, such as poly(2,3-dimethylbutadiene), polyisoprene, polyacetylenes and polycylopenta- and -hexadiene; polymers having C—C-triple bonds, such as polydiacetylenes; polymers having aromatic groups, such as polystyrene, terpolymers of acrylonitrile, butadiene and styrene, and copolymers of styrene and acrylonitrile; polymers having C—N-triple bonds, such as polyacrylonitrile, polyacrylonitrile-copolymers with e.g. vinyl chloride, vinylidene chloride, vinyl acetate or (meth)acrylic acid esters or mixtures of two or more thereof as comonomers; polymers having C—O-double bonds, such as polyesters, polyacrylamides, poly(acrylic acids), polyurea and polyketones; polymers having C—S-double bonds, such as polysulfones and polyethersulfones; halogen-containing polymers, such as poly(vinyl chloride) and poly(vinylidene chloride); and polymers containing nitro groups, which may be obtained by nitration of e.g. polyolefins by means of polymer analogous reactions.

Examples for polymers being preferably used within the present invention include polyisoprene, polybutadiene, ethylene/CO-copolymers, propylene/CO-copolymers, poly (methyl(meth) acrylate), polyterephthalate, polyadipate, etc..

Generally, a complete reaction of the introduced educts is achieved. However, the reaction, preferably hydrogenation, may be also carried out in such a way that by suitably choosing temperature, e.g. $H_2$-pressure and $H_2$-amount only one kind of e.g. groups to be hydrogenated may be reacted, while the other kind of e.g. groups to be hydrogenated are not hydrogenated.

The process of the invention is particularly suitable for reacting, preferably hydrogenating, polymers comprising units of different structure, as defined above, e.g. a polymer comprising C—C-multiple bonds and C=O-groups, since the catalyst of the present invention is capable to first selectively react the C—C multiple bond, e.g. to achieve a hydrogenation of these groups of about 90 to 100%, while at the same time the C=O-groups are reacted, e.g. hydrogenated to an extent of less than 25% and in general 0 to about 7%.

After finishing this reaction, preferably hydrogenation of the C—C-multiple bonds, it is of course possible to nearly quantitatively react, preferably hydrogenate, the other unsaturated groups being present in the polymer, e.g. C=O-groups by further introducing hydrogen.

The process of the invention may be used for already isolated and living polymers.

CATALYSTS

The process of the present invention is carried out in the presence of a catalyst which comprises a homogeneous ruthenium compound deposited in situ on a support. The catalyst of the present invention may be prepared by introducing a homogeneous ruthenium compound into a reactor together with the organic compound during the reaction so that the ruthenium compound deposits during the reaction on a support present in the reactor.

It is also possible for the homogeneous ruthenium compound to be introduced into the reactor before the reaction and to deposit on a support present in the reactor during the reaction.

The term "in situ" used in the context of the present application means that the catalyst is not prepared and dried separately and then introduced into the reactor as a finished catalyst, but that, for the purposes of the present invention, the catalyst is formed in the reactor either directly before or during the actual reaction.

The term "homogeneous ruthenium compound" used in the context of the present application means that the ruthenium compound used according to the present invention is soluble in the surrounding medium, ie. the aromatic compound still to be hydrogenated or in a mixture of these compounds with at least one solvent.

Ruthenium compounds used here are in particular nitrosyl nitrates and nitrates, but also halides, carbonates, carboxylates, acetylacetonates, chloro, nitrido and amine complexes and also hydrated oxides or mixtures thereof. Preferred compounds are ruthenium nitrosyl nitrate, ruthenium(III) chloride, ruthenium(III) nitrate and hydrated ruthenium oxide.

Although the amount of the ruthenium compound applied to the support or supports for the purposes of the process of the present invention is not restricted in any particular way, from the point of view of sufficient catalytic activity and the economics of the process the ruthenium salt or the ruthenium complex is applied to the support or supports in such amounts that from 0.01 to 30% by weight, based on the total weight of the catalyst, of ruthenium is deposited on the support or supports. This amount is more preferably from 0.2 to 15% by weight, particularly preferably about 0.5% by weight.

SUPPORTS

The geometric form of the support and the catalyst, respectively, is not particularly limited and may be varied in broad ranges. The support/catalyst may be present in the form of a structurized cloth packing, as a monolith, a ring, a helix etc..

The supports present in the reactor are preferably metal meshes and metal rings or steatite bodies, as described e.g. in EP-A-0 564 830 and EP-A-0 198 435. In the following, the supports which are particularly preferably used within the present invention and their preparation is discussed.

Particularly preferably metal support materials, such as refined steels having the material numbers 1.4767, 1.4401, 2.4610, 1.4765, 1.4847, 1.4301, etc. are used, since their surfaces may be roughened by tempering prior to the coating with the active components. Particularly preferably used as the mesh material is Kanthal (material number 1.4767) or metals containing aluminum. Kanthal is an alloy comprising about 75% by weight of Fe, about 20% by weight of Cr and about 5% by weight of Al. For the tempering, the above-mentioned metallic supports are heated in the presence of air at temperatures of 600 to 1100, preferably 800 to 1000° C. for 1 to 20, preferably 1 to 10 hours, and are subsequently cooled down. This pre-treatment is described in EP-A-0 564 830 and essential for the activity of the catalyst, since without this tempering treatment practically no ruthenium may be deposited in situ on the metallic support. After this treatment of the support at elevated temperature, the support is either coated with the ruthenium compound or directly inserted in the reactor.

In a further preferred embodiment, a layer of a palladium metal such as Ni, Pd, Pt, Rh, preferably Pd may be vapor deposited on the above-described support in a thickness of about 0.5 to about 10 nm, particularly about 5 nm, as also described in the above-mentioned EP-A-0 564 830. Furthermore, the above-mentioned metal of the VIII. side group of the periodic table (palladium metal) may be also deposited by means of impregnation. The metal content is in general about 1 to about 5%, based on the support surface.

In order to influence their catalytic properties, the catalysts according to the invention or as used according to the invention may be promoted with one or more other metals, particularly those of the I., VI., VII., or VIII. side group of the periodic table, chromium, iron, cobalt, tantalum, molybdenum, iridium, rhenium and the above-mentioned platinum metals being in particular to be mentioned. In general, the content of these promoters on the catalyst is about 0.01 to about 15 weight percent, preferably about 0.1 to about 5 weight percent, based on the total weight of the catalyst.

As may be deduced from the examples according to the invention, within the present invention, particularly a mesh of tempered Kanthal having a layer of palladium having a thickness of about 5 nm vapor deposited there onto, is used as a support.

However, it is also possible to use customary catalyst support systems such as activated carbon, silicon carbide, aluminum oxide, silicon dioxide, titanium dioxide, zirconium dioxide, magnesium oxide, zinc oxide or mixtures thereof, in each case in sphere, extrudate or ring form. Among these, particular preference is given to aluminum oxide and zirconium dioxide. The pore size and the pore size distribution of these supports is not at all critical. Et is possible to use bimodal and all other types of supports. The supports are preferably macroporous.

The catalysts used according to the present invention display a high reactivity (high turnover number), selectivity and operating life. In the reaction using the catalysts of the present invention, the reaction products are obtained in high yield and purity, with subsequent purification being superfluous. The conversion is virtually quantitative; the e.g. residual aromatic content is preferably below 0.01% by weight, based on the total amount of product. The reaction product obtained can, in a preferred embodiment of the present invention, thus be fed directly to further processing without having to be purified.

As may be deduced from the above, the present invention also relates to a supported catalyst obtainable by a process wherein a homogeneous ruthenium compound or a mixture of two or more thereof is deposited on a support by passing a solution comprising the ruthenium compound or the mixture of two or more thereof through said support or along the same.

FIG. 1 shows a transmission electron-microscopy picture of the catalyst of the invention. As may be deduced therefrom, the catalyst of the invention exhibits with respect to the deposited ruthenium a high porosity, said porosity being higher than the porosity of ruthenium being deposited on such a support by means of a commonly used process, such as impregnation. Without being bound to a particular theory, this specific structure seems to be responsible for the advantageous properties of the catalyst of the invention.

The difference in structure of a metal being deposited on a support by impregnation and of a metal being deposited as outlined above with respect to the catalyst of the invention is also directly apparent from FIG. 1 when comparing the structure of the Pd-layer being deposited by impregnation with the Ru-layer.

SOLVENTS OR DILUENTS

In the process of the present invention, the catalytic reaction can be carried out in the absence of a solvent or diluent, ie. it is not necessary to carry out the reaction in solution.

However, preference is given to using a solvent or diluent. Any suitable solvent or diluent can be used; the selection is not critical. For example, the solvents or diluents can also contain small amounts of water.

For the reaction of an aromatic compound in which at least one hydroxyl group is bonded to an aromatic ring, examples of suitable solvents or diluents are as follows:
straight-chain or cyclic ethers such as tetrahydrofuran or dioxane, and also aliphatic alcohols in which the alkyl radical preferably has from 1 to 10 carbon atoms, in particular from 3 to 6 carbon atoms.

Examples of preferred alcohols are i-propanol, n-butanol, i-butanol and n-hexanol.

Mixtures of these or other solvents or diluents can likewise be used.

For the reaction of an aromatic compound in which at least one amino group is bonded to an aromatic ring, examples of suitable solvents or diluents are as follows:
straight-chain or cyclic ethers such as tetrahydrofuran or dioxane, and also ammonia and monoalkylamines or dialkylamines in which the alkyl radical preferably has from 1 to 3 carbon atoms.

Mixtures of these or other solvents or diluents can likewise be used.

In both the above embodiments, the amount of solvent or diluent used is not restricted in any particular way and can be freely chosen as required, although preference is given to amounts which lead to a solution of the compound to be hydrogenated having a concentration of from 10 to 70% by weight.

In the process of the present invention, particular preference is given to using the product formed in the reaction of this process as solvent, if desired in addition to other solvents or diluents. In this case, part of the product formed in the process can be mixed into the compounds to be reacted.. The amount of product mixed in as solvent or diluent is preferably from 1 to 30 times, particular preferably from 5 to 20 times, in particular from 5 to 10 times, the weight of the organic compounds to be reacted.

The above statements do also apply for the other compounds which are reacted according to the invention, i.e. also with respect to these compounds no limitation with respect to the solvent or dilient exist.

REACTION

In the following, the reaction is described by means of an example for the hydrogenation. In case a dehydrogenation or an oxidation should be carried out, instead of hydrogen or a hydrogen containing gas, gaseous carbohydrates or oxygen containing gases may be used under the below described conditions.

The hydrogenation is carried out at appropriate pressures and temperatures. Preference is given to pressures above 50 bar, preferably from 100 to 300 bar. Preferred temperatures are in a range from 50 to 250° C., preferably from 150 to 220° C.

The hydrogenation process can be carried out continuously or as a batch process. In the continuous process, part of the hydrogenation product leaving the reactor can be recirculated to the reactor feed upstream of the reactor. The amount of the hydrogenation product leaving the reactor which is recirculated as solvent is such that the ratios specified in the section "Solvents and Diluents" are achieved. The remaining amount of hydrogenation product is taken off.

In the continuous process procedure, the amount of the compound or compounds to be hydrogenated is preferably from about 0.05 to about 3 l per liter of catalyst per hour, more preferably from about 0.1 to about 1 l per liter of catalyst per hour.

As hydrogenation gases, it is possible to use any gases which contain free hydrogen and do not contain any harmful amounts of catalyst poisons such as CO. For example, reformer off-gases can be used. Preference is given to using pure hydrogen as hydrogenation gases.

In the case of the phenols and amines additionally substituted by at least one unsubstituted or substituted $C_1$–$C_{10}$-alkyl and/or $C_1$–$C_{10}$-alkoxy radical, the resulting isomer ratio of cis to trans products can be varied within a wide range depending on the reaction conditions (temperature, solvent).

If an aromatic compound in which at least one amino group is bonded to an aromatic ring is to be hydrogenated by means of the catalyst of the present invention, the hydrogenation is preferably carried out in the presence of ammonia or monoalkylamines or dialkylamines, for example methylamine, ethylamine, propylamine or dimethylamine, diethylamine or dipropylamine. The amounts of ammonia or monoalkylamines or dialkylamines used are preferably from about 0.5 to about 50 parts by weight, particularly preferably from about 1 to about 20 parts by weight, in each case based on 100 parts by weight of the compound or compounds to be hydrogenated. Particular preference is given to using anhydrous ammonia or anhydrous amines.

For oxidations in general air or pure oxygen is used. For dehydrogenations the commonly used carbohydrates, particularly methane or natural gas are used.

The invention is illustrated below by means of some examples. Examples 1 to 6 relate to the hydrogenation of an aromatic compound in which at least one hydroxyl group is bonded to an aromatic ring, Examples 7 to 15 relate to the hydrogenation of an aromatic compound in which at least one amino group is bonded to an aromatic ring and examples 16 to 20 relate to the hydrogenation of aldehydes, ketones, and esters.

EXAMPLE 1

A Kanthal mesh onto which a Pd layer having a thickness of 50 nm had been vapor deposited and having a mesh diameter of 1 mm was installed in a 3.5 l autoclave. In the first run, 2000 ml of p-tert-butylphenol together with 200 mg of ruthenium nitrosyl nitrate were placed in the autoclave. The mixture was subsequently hydrogenated for 60 minutes at 180° C. and a hydrogen pressure of 200 bar. The reaction product was colorless and free of traces of ruthenium. It comprised 98.5% of p-tert-butylcyclohexanol. In a second run, 2000 ml of p-tert-butylphenol were reacted with hydrogen in a similar manner but without further addition of ruthenium. The colorless reaction product was free of traces of ruthenium and comprised 99% of p-tert-butylcyclohexanol.

EXAMPLE 2

The hydrogenation was carried out using a method similar to Example 1. The ruthenium compound used was hydrated ruthenium oxide. The clear reaction product was free of p-tert-butylphenol and traces of ruthenium. It contained 96% of p-tert-butylcyclohexanol. Subsequently, a further 30 runs were carried out in the autoclave without further addition of ruthenium. Conversion and selectivity remained constant during all runs.

EXAMPLE 3

The hydrogenation was carried out using a method similar to Example 1. The phenol compound used was 50 g of bisphenol A dissolved in 100 ml of tetrahydrofuran and 50 mg of ruthenium nitrosyl nitrate were added. The reaction was carried out for 90 minutes at 200° C. and 200 bar of hydrogen pressure. The phenol compound used was completely reacted within this time at a selectivity of 98%.

EXAMPLE 4

120 g of steatite spheres which has previously been dipped in a 15% strength nitric acid/ruthenium nitrosyl nitrate solution were placed in a 3.5 l autoclave fitted with a basket insert of $V_2A$ steel. 2000 ml of p-tert-butylphenol were then added to the autoclave and the mixture was hydrogenated for 60 minutes at 180° C. and 200 bar of hydrogen pressure. The reaction product was colorless and free of traces of ruthenium. It comprised 97% of p-tert-butylcyclohexanol.

EXAMPLE 5

A 3 l tube reactor was filled with metal rings (diameter 3 mm; manufactured and sold by Raschig). At 180° C. and 200 bar of hydrogen pressure, 3000 ml of p-tert-butylphenol in which 500 mg of ruthenium nitrosyl nitrate had been dissolved were introduced into the reactor over a period of 60 minutes. Subsequently, 1500 ml/h of fresh p-tert-butylphenol without further addition of ruthenium were fed in. The conversion in the crude product was quantitative and the p-tert-butylcyclohexanol content was 98%.

EXAMPLE 6 p-tert-Butylphenol was hydrogenated using a method similar to Example 1 but using different ruthenium compounds. The Kanthal mesh had not had Pd vapor deposited on it beforehand. The results are shown in the following table:

| Compound | Conversion | Selectivity |
|---|---|---|
| $Ru(NO_3)_2$ | 95% | 97% |
| Ru(acac) | 92% | 96% |
| $RuCl_3$ | 85% | 97% |

EXAMPLE 7

A Kanthal mesh onto which a Pd layer having a thickness of 50 nm had been vapor deposited and having a mesh diameter of 1 mm was installed in a 3.5 l autoclave. 200 mg of ruthenium nitrosyl nitrate were dissolved in 2000 ml of aniline and added to the autoclave. The mixture was subsequently hydrogenated for 60 minutes at 180° C. and a hydrogen pressure of 200 bar. The reaction product was colorless and free of traces of ruthenium. It comprised 99.9% of cyclohexylamine. Subsequently, 2000 ml of aniline were reacted with hydrogen in the same autoclave without addition of ruthenium compounds. The colorless reaction product was free of traces of ruthenium and comprised 99.8% of cyclohexylamine.

EXAMPLE 8

The hydrogenation was carried out using a method similar to Example 7. Hydrated ruthenium oxide was used as ruthenium compound. The clear reaction product was free of aniline and traces of ruthenium. It comprised 96% of cyclohexylamine and 4% of dicyclohexylamine. Subsequently, a further 30 runs were carried out in the autoclave without further addition of ruthenium. Conversion and selectivity remained constant during all runs.

EXAMPLE 9

The hydrogenation was carried out using a method similar to Example 7. The amine compound used was 50 g of tolylenediamine dissolved in 100 ml of tetrahydrofuran and 50 mg of ruthenium nitrosyl nitrate were added. The mixture was reacted for 90 minutes at 200° C. and 200 bar of hydrogen pressure. The conversion was quantitative. The selectivity was 98%.

EXAMPLE 10

The hydrogenation was carried out using a method similar to Example 7. The amine compound used was methyleneditoluidine. The conversion was quantitative, the selectivity was 98%.

EXAMPLE 11

The hydrogenation was carried out using a method similar to Example 7. The amine compound used was 4,4'-methyleneditoluidine. The conversion was quantitative, the selectivity was 97%.

EXAMPLE 12

120 g of steatite spheres which has previously been dipped in a 15% strength nitric acid/ruthenium nitrosyl nitrate solution were placed in a 3.5 l autoclave fitted with a basket insert of $V_2A$ steel. 2000 ml of aniline were then added to the autoclave and the mixture was hydrogenated for 60 minutes at 180° C. and 200 bar of hydrogen pressure. The reaction product was colorless and free of traces of ruthenium. It comprised 99% of cyclohexylamine.

EXAMPLE 13

A 3 l tube reactor was filled with metal rings (diameter 3 mm; manufactured and sold by Raschig). At 180° C. and 200 bar of hydrogen pressure, 3000 ml of aniline in which 500 mg of ruthenium nitrosyl nitrate had been dissolved were introduced into the reactor over a period of 60 minutes. Subsequently, 1500 ml/h of fresh aniline without further addition of ruthenium were fed in. The conversion in the crude product was quantitative. The cyclohexylamine content was 99.5%.

EXAMPLE 14

3 l of steatite spheres were impregnated with a 15% strength nitric acid/ruthenium nitrosyl nitrate solution and subsequently treated with hydrogen at 200° C. The spheres thus prepared were placed in a 3l tube reactor and used as in Example 13 for hydrogenating aniline without further addition of ruthenium.

EXAMPLE 15

Aniline was hydrogenated using a method similar to Example 8 but using different ruthenium compounds. The results are shown in the following table.

| Compound | Conversion | Selectivity |
|---|---|---|
| $Ru(NO_3)_2$ | 95% | 97% |
| Ru(acac) | 92% | 96% |
| $RuCl_3$ | 85% | 97% |

The hydrogenation of the aldehydes, ketones and esters was carried out with the following catalyst:

Catalyst I

A cloth of refined steel having the material number 1.4767 composed of Fe, Cr and Al is purified in an ultrasonic bath wherein the adhering oils and fats are removed. Subsequently said cloth is heated at 900° C. in air in a muffle. The obtained cloth is partly deformed by means of a toothed wheel roll and subsequently the corrugated cloth is rolled together with an even piece of cloth. The cylindrical monolith as obtained was built in a continuously working hydrogenation reactor.

Catalyst II

A cloth of refined steel having the material number 1.4767 composed of Fe, Cr and Al is purified in a ultrasonic bath, wherein the adhering oils and fats are removed. Subsequently, the cloth is heated at 900° C. in the air for 5 hours in a muffle. After cooling, a palladium layer having a thickness of 4 nm is vapor deposited on both sides of the cloth by means of a continuously working electron beam vaporization device (layer thickness was measured by means of a swinging quartz).

The obtained cloth was partly deformed by means of a toothed wheel roll and subsequently the corrugated cloth was rolled with an even piece of cloth. The obtained cylindrical monolith was built in a continuously working hydrogenation reactor.

EXAMPLE 16

Catalyst I in the form of rolls of metal mesh was built in a tube reactor (length=2500 nm, dia=45 nm). Subsequently, the reactor was filled with n-butanol and was heated to 180° C. at a hydrogen pressure of $3 \cdot 10^6$ Pa (30 bar). Then, an amount of 1 kg/h n-butylalderhyde was continuously introduced into the reactor with a flow amount of 50 l/h. In the first 5l butylalderhyde 13 g ruthenium nitrosylnitrate were present. The obtained reaction product was colorless and free from ruthenium.

A conversion of 99.4% and a selectivity with respect to n-butanol of 99.7, respectively based on the introduced amount of n-butylalderhyde, was determined by gas chromotagraphic evaluation.

EXAMPLE 17

A metal mesh with catalyst II (about 40.000 $cm^3$), 700 g of a copolymer of ethylene and CO ($M_w$ 5000, CO content 35% percent), dissolved in 1300 g THF and 500 mg ruthenium nitrosylnitrate were introduced in a 3.5l-autoklav.

Subsequently, the mixture was hydrogenated at 180° C. and $2 \cdot 10^7$ Pa (200 bar) hydrogen pressure for 5 hours. The conversions to the desired polyalcohol was 93%, based on the introduced amount of the copolymer.

EXAMPLE 18

A metal mesh comprising catalyst II was inserted in a 3.5l-autoklav, and 2000 g benzaldehyde and 500 mg ruthenium nitrosylnitrate were introduced there into. Subsequently the mixture was hydrogenated at 180° C. and 2·10⁷ Pa (200 bar) hydrogen pressure for 10 hours. The conversion to the desired cyclohexyl methanol was 100% at a selectivity of 96.5%, based on the introduced amount of benzaldehyde, respectively.

EXAMPLE 19

Catalyst II was inserted in a 3.5l-autoklav and 2000g and 2-ethylhexanaol and 500 mg ruthenium nitrosylnitrate were introduced there into. Subsequently, the mixture was hydrogenated at 180° C. and 2·10⁷ Pa (200 bar) hydrogen pressure for 10 hours. The conversion to the desired 2-ethylhexanol was 100% at a selectivity of 97.2%, based on the introduced amount of 2-ethylhexanol, respectively.

EXAMPLE 20

In a 0.3l-stirring autoklav, 100 ml adipodimethylester was reacted at a metal mesh and 100 mg ruthenium (III) acetylacetonate. The mixture was stirred for 12 hours at a hydrogen pressure of 2·10⁷ Pa (200 bar) and a temperature of 220° C. A conversion of 98% and a yield with respect to hexandiol of 91% based on the introduced amount of adipodimethylester was determined by a gaschromatic analysis of the obtained product.

We claim:

1. A process for reacting an organic compound in the presence of a catalyst comprising a homogeneous ruthenium compound or a mixture of two or more thereof deposited in situ on a support, wherein the homogeneous ruthenium compound is introduced into a reactor together with the organic compound and said homogeneous ruthenium compound is deposited on a support present in the reactor during the reaction.

2. The process defined in claim 1, wherein the reaction is a hydrogenation, dehydrogenation, hydrogenolysis, aminating hydrogenation or dehalogenation.

3. The process defined in claim 1, wherein the organic compound is selected from the group consisting of an aromatic compound in which at least one hydroxyl group is bonded to the aromatic ring, an aromatic compound in which at least one amino group is bonded to the aromatic ring, a ketone, an aldehyd, a carboxylic acid or a derivative thereof, a polymer comprising at least one C—C double bond, a polymer comprising at least one C=O-group, and a mixture of two or more thereof.

4. The process defined in claim 1, wherein the support is selected from the group consisting of a metal mesh, a metal ring, a steatite body, activated carbon, silicon carbide, aluminum oxide, silicon dioxide, titanium dioxide, zirconium dioxide, magnesium oxide, zinc oxide or a mixture of two or more thereof, in each case in sphere, extrudate or ring form.

5. The process defined in claim 1, wherein the support is a metal mesh comprising aluminum, a metal mesh onto which a palladium metal layer has been vapor-deposited in a thickness of from 0.5 to 10 nm, or a metal mesh comprising aluminum onto which a palladium metal layer has been vapor-deposited in a thickness of from 0.5 to 10 nm.

6. The process defined in claim 1, wherein the homogeneous ruthenium compound is selected from the group consisting of nitrosyl nitrates, nitrates, halides, carbonates, acetylacetonates, chloro, nitrido and amine complexes, and also hydrated oxides of ruthenium, and a mixture of two or more thereof.

7. The process defined in claim 1, wherein the reaction is carried out in the presence of a solvent or diluent.

8. A supported catalyst, obtainable by a process wherein a homogeneous ruthenium compound or a mixture of two or more thereof is deposited on a support while passing a solution comprising the ruthenium compound or the mixture of two or more thereof through said support or along the same.

9. A process for reacting an organic compound in the presence of a catalyst comprising a homogeneous ruthenium compound or a mixture of two or more thereof deposited in situ on a support, wherein the homogeneous ruthenium compound is introduced into a reactor prior to the reaction and said homogeneous ruthenium compound is deposited on a support present in the reactor during the reaction.

10. The process defined in claim 9, wherein the reaction is a hydrogenation, dehydrogenation, hydrogenolysis, aminating hydrogenation or dehalogenation.

11. The process defined in claim 9, wherein the organic compound is selected from the group consisting of an aromatic compound in which at least one hydroxyl group is bonded to the aromatic ring, an aromatic compound in which at least one amino group is bonded to the aromatic ring, a ketone, an aldehyd, a carboxylic acid or a derivative thereof, a polymer comprising at least one C—C double bond, a polymer comprising at least one C=O-group, and a mixture of two or more thereof.

12. The process defined in claim 9, wherein the support is selected from the group consisting of a metal mesh, a metal ring, a steatite body, activated carbon, silicon carbide, aluminum oxide, silicon dioxide, titanium dioxide, zirconium dioxide, magnesium oxide, zinc oxide or a mixture of two or more thereof, in each case in sphere, extrudate or ring form.

13. The process defined in claim 9, wherein the support is a metal mesh comprising aluminum, a metal mesh onto which a palladium metal layer has been vapor-deposited in a thickness of from 0.5 to 10 nm, or a metal mesh comprising aluminum onto which a palladium metal layer has been vapor-deposited in a thickness of from 0.5 to 10 nm.

14. The process defined in claim 9, wherein the homogeneous ruthenium compound is selected from the group consisting of nitrosyl nitrates, nitrates halides, carbonates acetylacetonates, chloro, nitrido and amine complexes and also hydrated oxides of ruthenium, and a mixture of two or more thereof.

15. The process defined in claim 9, wherein the reaction is carried out in the presence of a solvent or diluent.

* * * * *